(12) United States Patent
Roy et al.

(10) Patent No.: US 9,157,886 B2
(45) Date of Patent: Oct. 13, 2015

(54) FLEXIBLE AMINE SENSOR BASED ON ULTRATHIN POLY-THIOPHENE THIN FILM TRANSISTOR

(75) Inventors: Vellaisamy A. L. Roy, Hong Kong (CN); Zong-Xiang Xu, Hong Kong (CN)

(73) Assignee: CITY UNIVERSITY OF HONG KONG, Hong Kong (CN)

( * ) Notice: Subject to any disclaimer, the term of this patent is extended or adjusted under 35 U.S.C. 154(b) by 679 days.

(21) Appl. No.: 13/152,816

(22) Filed: Jun. 3, 2011

(65) Prior Publication Data

US 2012/0304741 A1    Dec. 6, 2012

(51) Int. Cl.
*G01N 7/00* (2006.01)
*G01N 27/414* (2006.01)
G01N 27/12 (2006.01)
H01L 51/00 (2006.01)
H01L 51/05 (2006.01)

(52) U.S. Cl.
CPC ............ *G01N 27/4145* (2013.01); *G01N 27/12* (2013.01); *G01N 27/127* (2013.01); *G01N 27/4141* (2013.01); *H01L 51/0036* (2013.01); *H01L 51/0545* (2013.01)

(58) Field of Classification Search
CPC .............. G01N 27/414; G01N 27/127; G01N 72/4141; G01N 27/12
USPC ......................................................... 73/31.06
See application file for complete search history.

(56) References Cited

U.S. PATENT DOCUMENTS

| | | | |
|---|---|---|---|
| 2003/0143112 A1* | 7/2003 | Suslick et al. | 422/55 |
| 2003/0166298 A1* | 9/2003 | Suslick | 436/169 |
| 2006/0231882 A1* | 10/2006 | Kim et al. | 257/310 |
| 2007/0012349 A1* | 1/2007 | Gaudiana et al. | 136/244 |
| 2010/0171417 A1* | 7/2010 | Kitamura et al. | 313/504 |

* cited by examiner

*Primary Examiner* — Hezron E Williams
*Assistant Examiner* — Rodney T Frank
(74) *Attorney, Agent, or Firm* — Amin, Turocy & Watson, LLP

(57) ABSTRACT

The design and fabrication of ultrathin poly-3-hexyl thiophene (P3HT) film based amine sensors are described herein. Ultrathin P3HT monolayer films can be built on a patterned flexible n-octadecylphosphonic acid (ODPA)/$Al_2O_3$/PET substrate, forming a flexible polymer thin film transistor according to a solution process. The mechanism of the sensor is based on the interaction of amine molecules with the surface of the P3HT monolayer. The interaction of amine molecules with the surface of the P3HT monolayer can affect the current density of the PTFT, and the change in current density can indicate the presence of amine molecules in the surroundings. The amine sensors described herein can easily detect amine molecules in a parts per billion (ppb) range. The amine sensors can be utilized, for example, as disposable sensors within food packaging to ensure the safety of the packaged food.

21 Claims, 7 Drawing Sheets

US 9,157,886 B2

FLEXIBLE AMINE SENSOR BASED ON ULTRATHIN POLY-THIOPHENE THIN FILM TRANSISTOR

TECHNICAL FIELD

This disclosure generally relates to the development and fabrication of flexible polymer thin film transistor (PTFT) amine sensors.

BACKGROUND

Neutral biogenic amines are important molecules in living systems, impacting many areas ranging from biomarkers of diseases to quality control of foodstuffs. Biogenic amines, such as histamine, spermidine, putrescine, and trimethylamine, are the key compounds in living systems and are involved in many vital biological functions, such as protein synthesis, regulation of cell proliferation, and modulation of gene expression.

Biogenic amines can be markers of biological disorders. For example, a high plasma level of putrescine and spermidine is associated with various cancers. Similarly, a wide range of biogenic agents have been found to be biomarkers for spoiled food. For example, an increase in histamine and other biogenic amines can indicate that food is beginning to spoil.

Since biogenic amines can be biomarkers useful for clinical diagnoses and food quality control, the detection of biogenic amines is of particular interest. For example, the detection of biogenic amine vapors that can build up as food spoils can be a valuable tool with regard to food quality control. Traditional methods of detecting biogenic amines include enzyme sensors, antibody sensors, and array sensors. However, these types of sensors are not good candidates for use in food quality control applications where cheap, disposable sensors are necessary. Supramolecular sensors, such as polymer thin film transistors (PTFTs) are easy and inexpensive to fabricate, making them excellent candidates for disposable sensors. However, the detection of neutral molecules, such as biogenic amines, through supramolecular sensors has traditionally been difficult.

The foregoing description is merely intended to provide an overview of some of the conventional sensors that can detect biogenic amines, and is not intended to be exhaustive. Problems with the state of the art and corresponding benefits of some of the various non-limiting embodiments may become further apparent upon review of the following detailed description.

SUMMARY

The following presents a simplified summary of the various embodiments in order to provide a basic understanding of some aspects described herein. This summary is not an extensive overview of the disclosed subject matter. It is intended to neither identify key or critical elements of the disclosed subject matter nor delineate the scope of the subject embodiments. Its sole purpose is to present some concepts of the disclosed subject matter in a simplified form as a prelude to the more detailed description that is presented later.

Various non-limiting embodiments are directed to the design of flexible polymer thin film transistors (PTFTs) that can sense amine vapors with a high sensitivity. The PTFT can be an ultrathin poly-3-hexyl thiophene (P3HT) film monolayer on a patterned flexible n-octadecylphosphonic acid (ODPA)/$Al_2O_3$/PET substrate. Ultrathin P3HT has a high charge mobility, facilitating the mechanism of action of the sensor, which can be due to the interaction of amine molecules with the surface of the P3HT monolayer. The interaction can affect the current density of the PTFT, and the change in current density can indicate the presence of amine molecules in the surroundings with high sensitivity (e.g., on the order of parts per billion (ppb)).

Methods are also provided for the fabrication of flexible PTFT amine sensors. The methods can include fabricating a bilayer ODPA/$Al_2O_3$ dielectric. The bilayer dielectric can be formed at a low temperature, for example, room temperature. The ODPA/$Al_2O_3$ can be deposited on a PET substrate. The method can also include forming the ultrathin P3HT film monolayer on the ODPA/$Al_2O_3$/PET substrate via a solution process. For example, P3HT can be dissolved in dichlorobenzene and the resulting solution spin coated on patterned ODPA/$Al_2O_3$/PET substrates.

According to a further non-limiting embodiment, the flexible PTFT amine sensors fabricated according to the solution process can be utilized as disposable amine sensors. The disposable amine sensors can be, for example, utilized in food packaging applications (e.g., within food packaging as a food safety tag) to ensure the safety of the packaged food. The amine sensors can sense amine vapors that can indicate, for example, that the food within the packaging has spoiled.

The following description and the annexed drawings set forth in detail certain illustrative aspects of the disclosed subject matter. These aspects are indicative, however, of but a few of the various ways in which the principles of the various embodiments may be employed. The disclosed subject matter is intended to include all such aspects and their equivalents. Other advantages and distinctive features of the disclosed subject matter will become apparent from the following detailed description of the various embodiments when considered in conjunction with the drawings.

DETAILED DESCRIPTION

Various aspects relate to the design and fabrication of gas sensors (e.g., amine sensors) based on highly sensitive flexible polymer thin film transistors (PTFTs). The amine sensors can include a thin film polymer deposited on a low temperature process self-assembly monolayer/metal oxide dielectric. The thin film polymer can be deposited on the dielectric, for example, by a solution process, which can be controlled to achieve an ultrathin monolayer polymer film (e.g., a thickness on the order of nanometers). The ultrathin monolayer polymer film can lead to an amine sensor with improved charge carrier transport properties. The amine sensor, fabricated according to an easy and inexpensive process, can be utilized, for example, as a disposable sensor in food packaging to ensure the safety of the packaged food.

Figure 1:
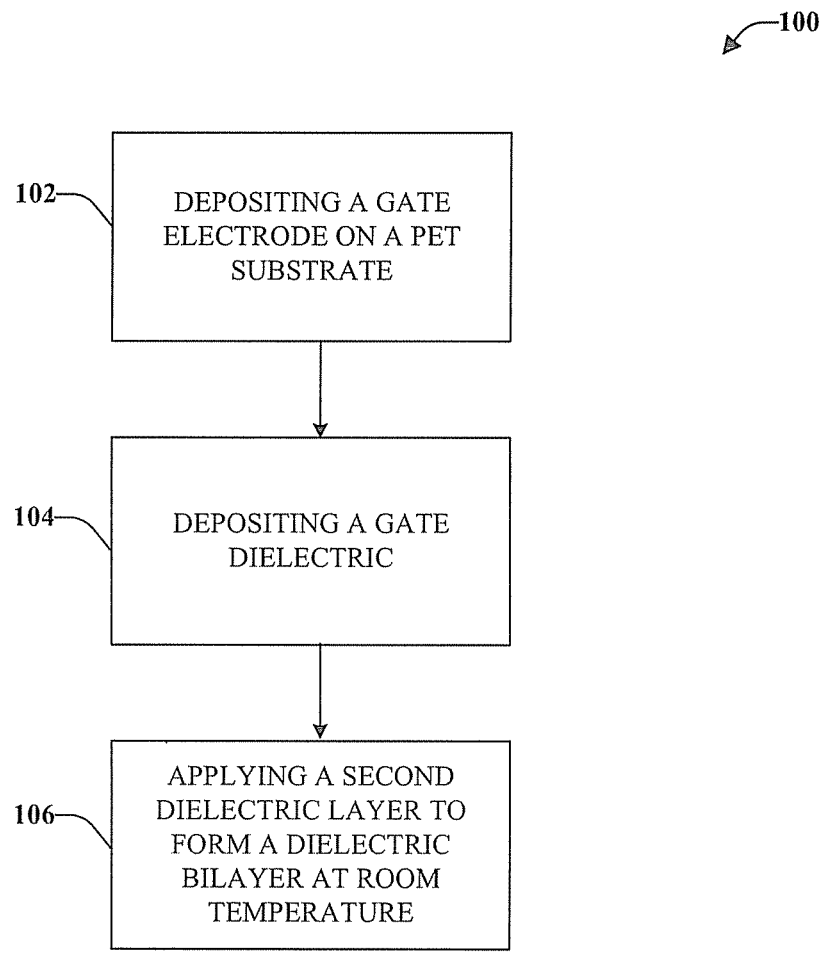
FIG. 1 is a schematic process flow diagram of a method for fabricating a substrate for an amine sensor.

Referring now to FIG. 1, illustrated is a schematic process flow diagram showing a method 100 for fabricating a substrate for a gas sensor (e.g., an amine sensor). At element 102, a gate electrode can be deposited onto a substrate. For example, the gate electrode can be an Ag gate electrode. The Ag gate electrode can be a 50-nm thick Ag film. The substrate can be a poly(ethylene terephthalate) (PET) substrate (e.g., a flexible PET substrate). The gate electrode can be deposited onto the substrate, for example, through a shadow mask by thermal evaporation.

At element 104, a gate dielectric can be deposited on the gate electrode and substrate. For example, the gate dielectric can be an $Al_2O_3$ layer. The $Al_2O_3$ layer can be a patterned 26-nm thick $Al_2O_3$ layer. The gate dielectric can be deposited on the substrate (e.g., Ag/PET substrate) by, for example, a Savannah 100 ALD system at a substrate temperature of 80° C.

At element 106, an octadecylphosphonic acid (ODPA) self-assembled monolayer (SAM) can be applied to the substrate after fabricating the gate dielectric. The ODPA SAM can be prepared, for example, by immersing the substrate in a 2-propanol solution containing 5 mM of ODPA. Keeping the solution at room temperature, the substrate can remain in the solution for a time period. For example, the time period can be 17 hours. After the period in solution, the substrates can be rinsed (e.g., by pure 2-propanol), blown dry (e.g., with nitrogen), and briefly baked (e.g., on a hotplate at 60° C. for 30 minutes). Accordingly, the bilayer ODPA/$Al_2O_3$ can be processed at a low temperature on PET substrates. This can create a patterned flexible bilayer ODPA/$Al_2O_3$/PET substrate.

Figure 2:
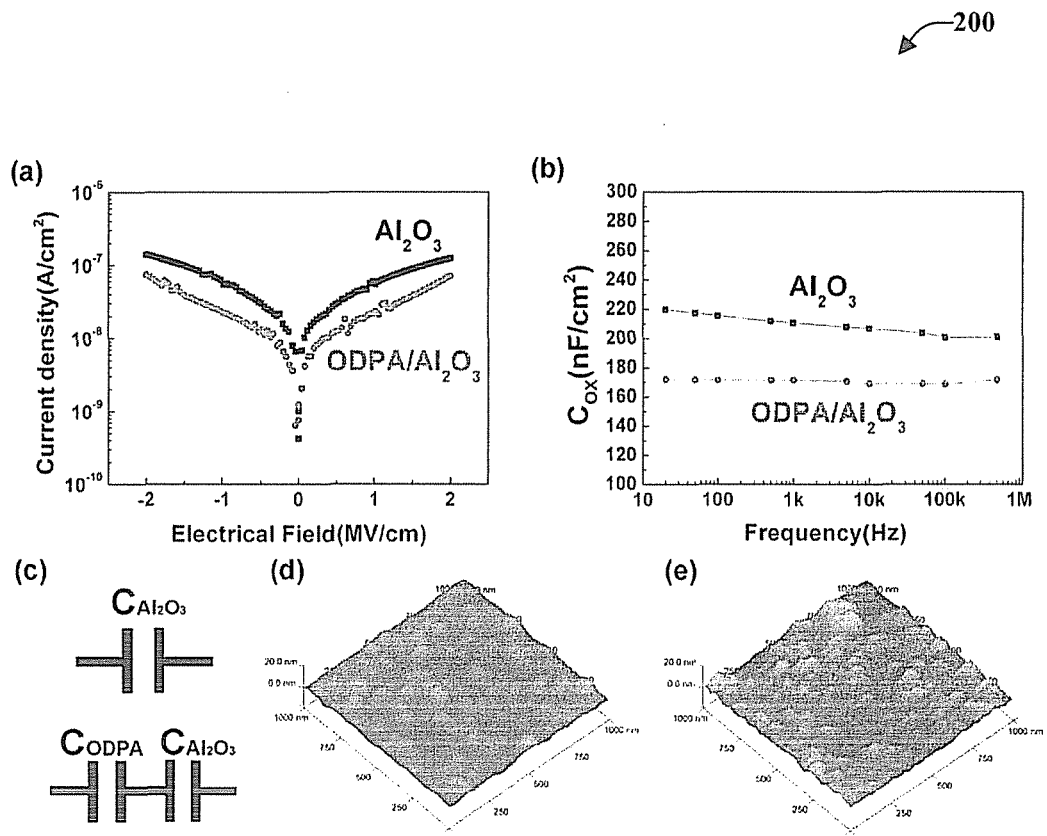
FIG. 2 illustrates characteristics of a substrate fabricated according to the method of FIG. 1.

Method 100 can produce an ODPA/$Al_2O_3$/PET substrate suitable for fabricating a gas sensor, such as an amine sensor. For example, the ODPA/$Al_2O_3$/PET substrate can exhibit a stable capacitance across a large range of frequencies. For example, the range of stable capacitance can be between 20 Hz and 600 kHz. Performance and mechanical properties of ODPA/$Al_2O_3$ were found to be superior to both $Al_2O_3$ alone and $SiO_2$. For example, the ODPA/$Al_2O_3$/PET substrates can exhibit a leakage current density of $7\times10^{-8}$ A/cm$^2$ at an applied electrical field of 2 MV/cm and capacitance densities of approximately 172 nF/cm$^2$. FIG. 2 illustrates characteristics 200 of a substrate fabricated according to the process 100. The characteristics 200 show the suitability of the patterned flexible bilayer ODPA/$Al_2O_3$/PET substrate produced using process 100 for fabricating a gas sensor, such as an amine sensor.

Element (a) is a plot of current density versus electric field characteristics for $Al_2O_3$ and ODPA/$Al_2O_3$. Element (b) is a plot of capacitance density ($C_{ox}$) versus frequency characteristics for $Al_2O_3$ and ODPA/$Al_2O_3$. The capacitance for ODPA/$Al_2O_3$ was found to be stable over a wide range of frequencies. Element (c) is a capacitor model for $Al_2O_3$ and bilayer ODPA/$Al_2O_3$. Element (d) is a 3D tapping mode atomic force microscopy (AFM) height image of $Al_2O_3$. Element (e) is a 3D tapping mode AFM height image of a bilayer ODPA/$Al_2O_3$.

The bilayer ODPA/$Al_2O_3$ can be formed at a low temperature on the flexible PET substrate for gas sensor (e.g., amine sensor) fabrication. In gas sensors, this bilayer dielectric can help to enhance the mobility of a film (e.g., ultrathin poly-3-hexyl thiophene (P3HT) film). This can lead to a gas sensor with an improved performance (e.g., detecting gas molecules, such as amines, with high sensitivity).

Figure 3:
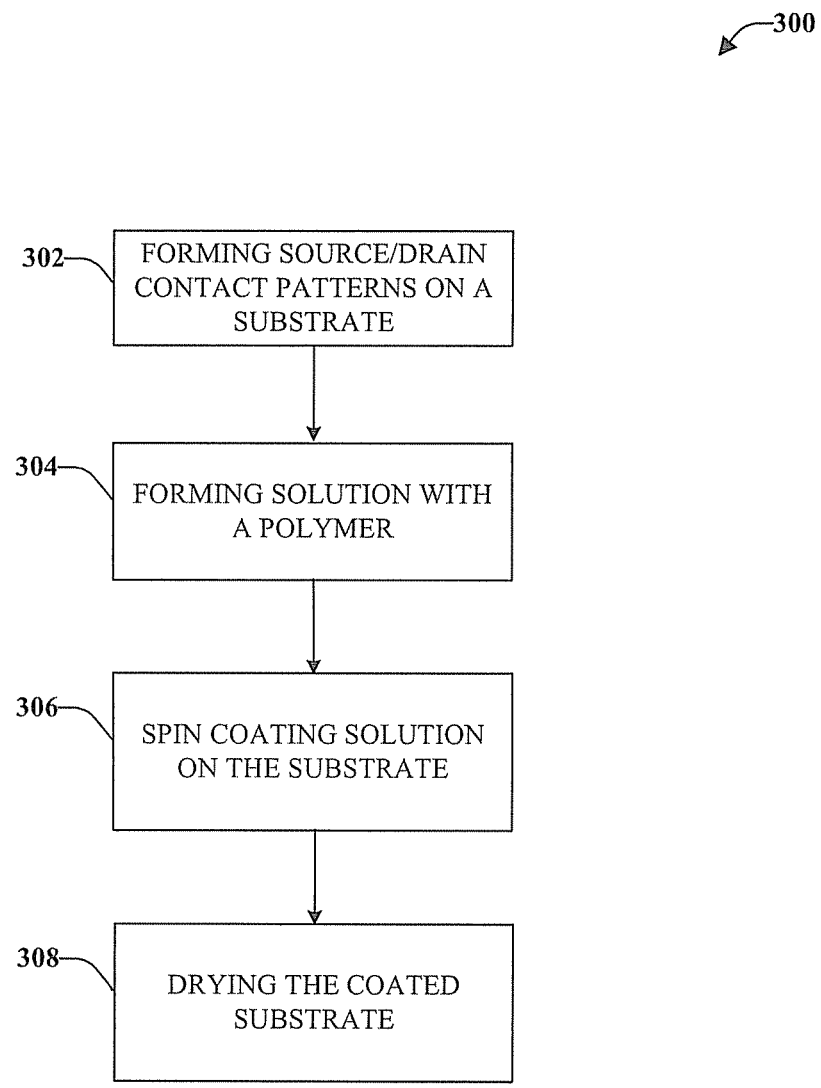
FIG. 3 is a schematic process flow diagram of a method for fabricating an ultrathin film polymer based amine sensor.

Referring now to FIG. 3, illustrated is a process flow diagram of a method 300 for fabricating an ultrathin film polymer based amine sensor. The ultrathin film polymer based amine sensor can be fabricated by depositing ultrathin film nanostructures of polymer on a low temperature processed self assembly monolayer/metal oxide dielectric to produce highly sensitive polymer thin film transistor (PTFT) based amine sensors.

At element 302, source/drain contact patterns are formed on a substrate. For example, the substrate can be a patterned flexible bilayer ODPA/$Al_2O_3$/PET substrate formed in accordance with method 100. The substrate can have a channel width W, for example, between approximately 1000 and approximately 3000 microns. The substrate can also have a channel width L, for example, between approximately 2 and approximately 100 microns. The source/drain contact patterns can be, for example, Ti/Au source/drain contact patterns. The source/drain contact patterns can be formed by image reversal photolithography followed by a standard lift-off process.

At element 304, a solution is formed including a polymer. For example, the polymer can be P3HT. The P3HT can be dissolved in dichlorobenzene, for example, by ultrasonic bath. At element 306, the solution (e.g., the P3HT dichlorobenzene solution) can be spin coated on the substrate. For example, the P3HT dichlorobenzene solution can be spin coated onto a patterned flexible bilayer ODPA/$Al_2O_3$/PET substrate with source/drain contact patterns formed at element 302. The spin speed can be, for example, with a spin speed of 2000 rpm/min. At element 308, the spin coated substrate can be dried. For example, the spin coated substrate can be annealed at 100° C. under a nitrogen atmosphere for twenty minutes. The polymer (e.g., P3HT) can be a conjugated polymer that forms an ultrathin monolayer crystalline polymer film through controlling the conditions of process 300. The ultrathin monolayer polymer film (e.g., with a thickness on the order of nanometers) can be prepared by the simple solution process as illustrated in method 300, on a low temperature processed substrate (e.g., a bilayer acid/metal oxide dielectric) to achieve a high sensitivity to amine molecules (e.g., sensitive on the order of parts per billion).

Figure 4:
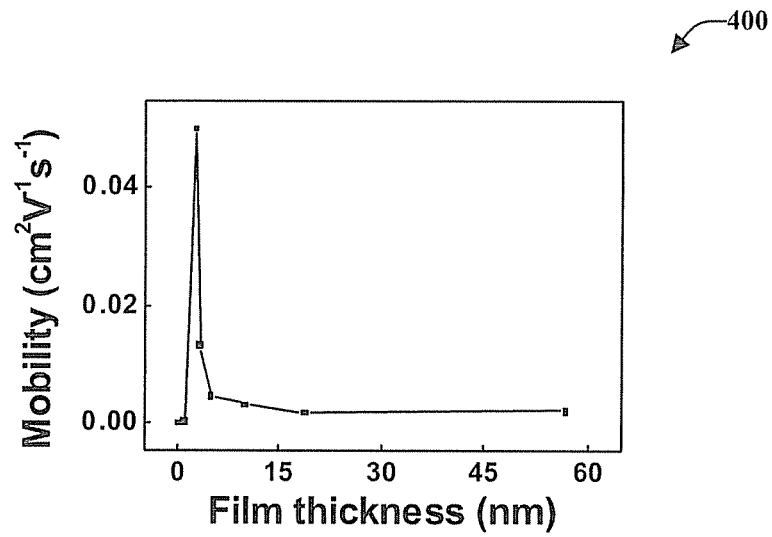
FIG. 4 is a plot illustrating the affect of polymer film thickness on mobility in amine sensors fabricated according to FIG. 3.

Referring now to FIG. 4, illustrated is a plot 400 showing the affect of polymer film thickness on mobility in amine sensors fabricated according to the method 300 of FIG. 3. Seven gas sensors were formed according to the method 300 of FIG. 3. At element 304, seven different concentrations of P3HT were dissolved in dichlorobenzene. The seven different concentrations were 0.25 mg/ml, 0.5 mg/ml, 1 mg/ml, 2.5 mg/ml, 5 mg/ml, 10 mg/ml, and 20 mg/ml respectively. The resulting solutions were spin coated onto ODPA/$Al_2O_3$/PET substrates according to element 306. After the spin coated substrates were dried according to element 308, seven sensors with varying film thicknesses based on the concentrations were produced. TABLE 1 illustrates the relationship between film thicknesses and concentration of P3HT.

TABLE 1

Film thicknesses in nm resulting from
P3HT concentrations utilized to fabricate thin
film transistor sensors according to a solution method.

| Concentration of P3HT (mg/ml) | Film Thickness (nm) |
|---|---|
| 0.25 | 1 |
| 0.5 | 2.5 |
| 1 | 3.2 |
| 2.5 | 4.9 |
| 5 | 9.9 |
| 10 | 18.8 |
| 20 | 56.5 |

Figure 5:
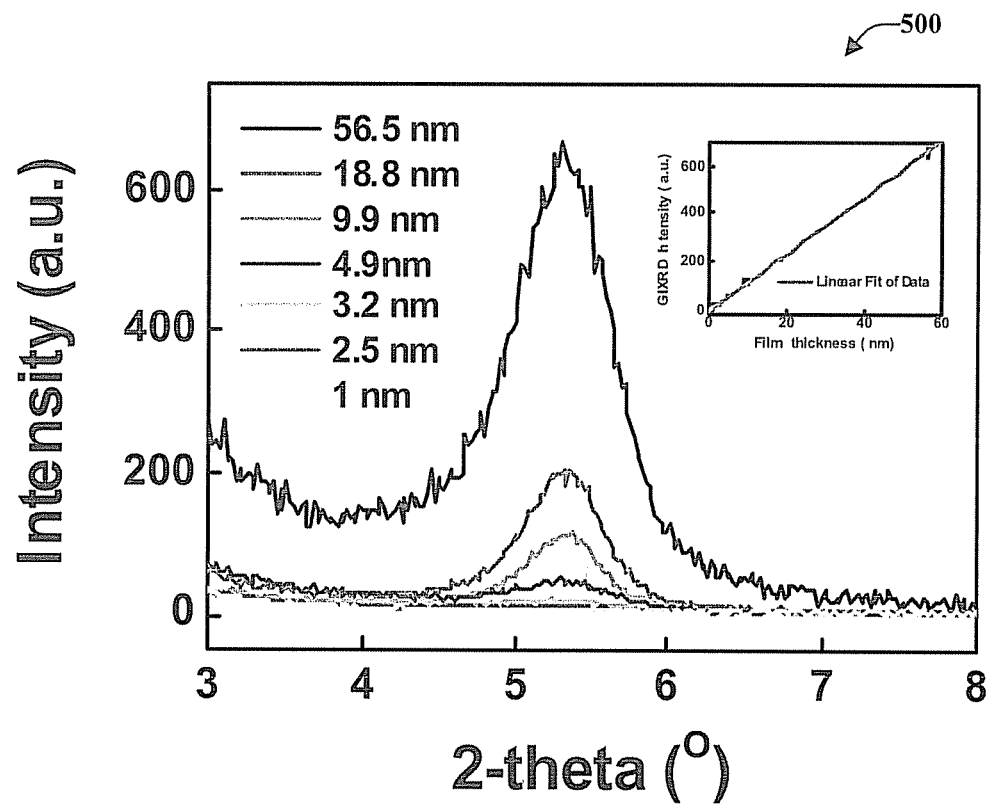
FIG. 5 is a plot illustrating the affect of polymer film thickness on GIXRD intensity for amine sensors fabricated according to FIG. 3.

The characteristics of the seven as-fabricated field effect transistor sensors were measured inside a N2 glove box (Mbraun MB20G) equipped with a probe station connected to a semiconductor parameter analyzer (Keithley 4200 SCS). The field effect charge mobility ($\mu$) was estimated from the output characteristics in the saturation region or the linear region (e.g., as illustrated in FIG. 5, which shows a plot of GIXRD intensity as a function of P3HT). As shown in FIG. 4, the field effect charge mobility for the sensors is the greatest when the film thickness is minimized (e.g., 2.5 nm as illustrated in plot 400). Accordingly, a particularly ultrathin monolayer polymer film, for example, with a thickness of approximately 2.5 nm, prepared by a simple solution process on a low temperature processed bilayer acid/metal oxide dielectric can be utilized in a PTFT amine sensor with high charge mobility.

For example, according to an embodiment, the thickness of the film is on the order of nanometers. In another embodiment, the thickness of the film can be between approximately one and approximately 60 nanometers. According to another embodiment, the thickness of the film can be between approximately 1 and approximately 15 nanometers. According to a further embodiment, the thickness of the film can be between approximately 1.5 and approximately 5.5 nanometers. In another embodiment, the thickness of the film can between approximately 2 and approximately 3 nanometers.

According to method 300, amine sensors based on P3HT can be fabricated on a patterned flexible bilayer ODPA/Al$_2$O$_3$/PET substrate according to a solution process. The sensor can detect amines, such as neutral biogenic amines, including histamine, spermidine, putrescine, trimethylamine, and the like. The mechanism for detecting amines is based on the interaction of amine molecules on the surface of the P3HT thin film monolayer. The interaction of amine molecules eventually affects the current density of the P3HT thin film monolayer transistor and indicates the presence of amine molecules in the surrounding area. For example, sensors fabricated according to method 300 can detect low levels of amine molecules (e.g., on the order of parts per billion). These sensors fabricated according to method 300 have applications, for example, in food packing to ensure the safety of the packed food.

Figure 6:
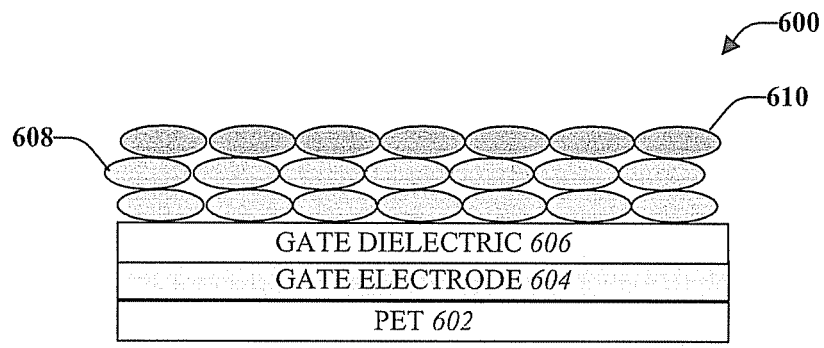
FIG. 6 is a schematic block diagram of an amine sensor.

Referring now to FIG. 6, illustrated is a schematic block diagram of an amine sensor 600. The amine sensor can be, for example, fabricated according to the solution method of FIG. 3 onto a substrate formed at a low temperature according to the method of FIG. 1.

The sensor can include a PET substrate 602. Formed on the PET substrate is a gate electrode 604. The gate electrode 604 can be, for example, an Ag gate electrode. Formed on the gate electrode can be a gate dielectric 606. The gate dielectric 606 can be, for example, an Al$_2$O$_3$ layer. Applied on top of the gate dielectric 606 is an ODPA self-assembled monolayer (SAM) layer 608. The ODPA 608 monolayer can be applied at a low temperature (e.g., room temperature). The PET substrate 602, gate electrode 604, gate dielectric 606 and ODPA monolayer 606 can create a patterned flexible bilayer ODPA/Al$_2$O$_3$/PET substrate.

Formed on the patterned flexible bilayer ODPA/Al$_2$O$_3$/PET substrate can be an ultrathin polymer layer 610. For example, the polymer can be P3HT, and the ultrathin polymer layer 610 can be formed on the substrate according to the solution process of method 300. The ultrathin polymer layer 610 can allow the sensor to achieve a high sensitivity to amine molecules (e.g., sensitive on the order of parts per billion). For example, according to an embodiment, the ultrathin polymer layer 610 can have a thickness is on the order of nanometers. In another embodiment, the ultrathin polymer layer 610 can have a thickness between approximately one and approximately 60 nanometers. According to another embodiment, the ultrathin polymer layer 610 can have a thickness between approximately 1 and approximately 15 nanometers. According to a further embodiment, the ultrathin polymer layer 610 can have a thickness between approximately 1.5 and approximately 5.5 nanometers. In another embodiment, the ultrathin polymer layer 610 can have a thickness between approximately 2 and approximately 3 nanometers.

The main significance of sensor 600 is the ultrathin polymer (e.g., P3HT) layer 610. The ultrathin polymer film layer 610 leads to an amine sensor with a high sensitivity for amine molecules and a high performance of the amine sensor. The high sensitivity and high performance can be due, for example, to the high charge carrier mobility of the ultrathin polymer film layer 610. High carrier mobility enhances the sensitivity of the sensor 600. Also significant is the low temperature processed patterned flexible bilayer ODPA/Al$_2$O$_3$/PET substrate. The substrate helps to enhance the mobility of the ultrathin polymer film 610 which can increase the mobility of the sensor 600. For example, the mobility of the sensor 600 can be 0.1 cm$^2$/Vs.

For example, sensor 600 can exhibit a sensitivity of less than 1000 parts per billion. According to a further example, sensor 600 can exhibit a sensitivity of less than 500 parts per billion. According to another example, sensor 600 can exhibit a sensitivity of less than 100 parts per billion. Further, for example, sensor 600 can exhibit a sensitivity of less than 50 parts per billion.

Figure 7:
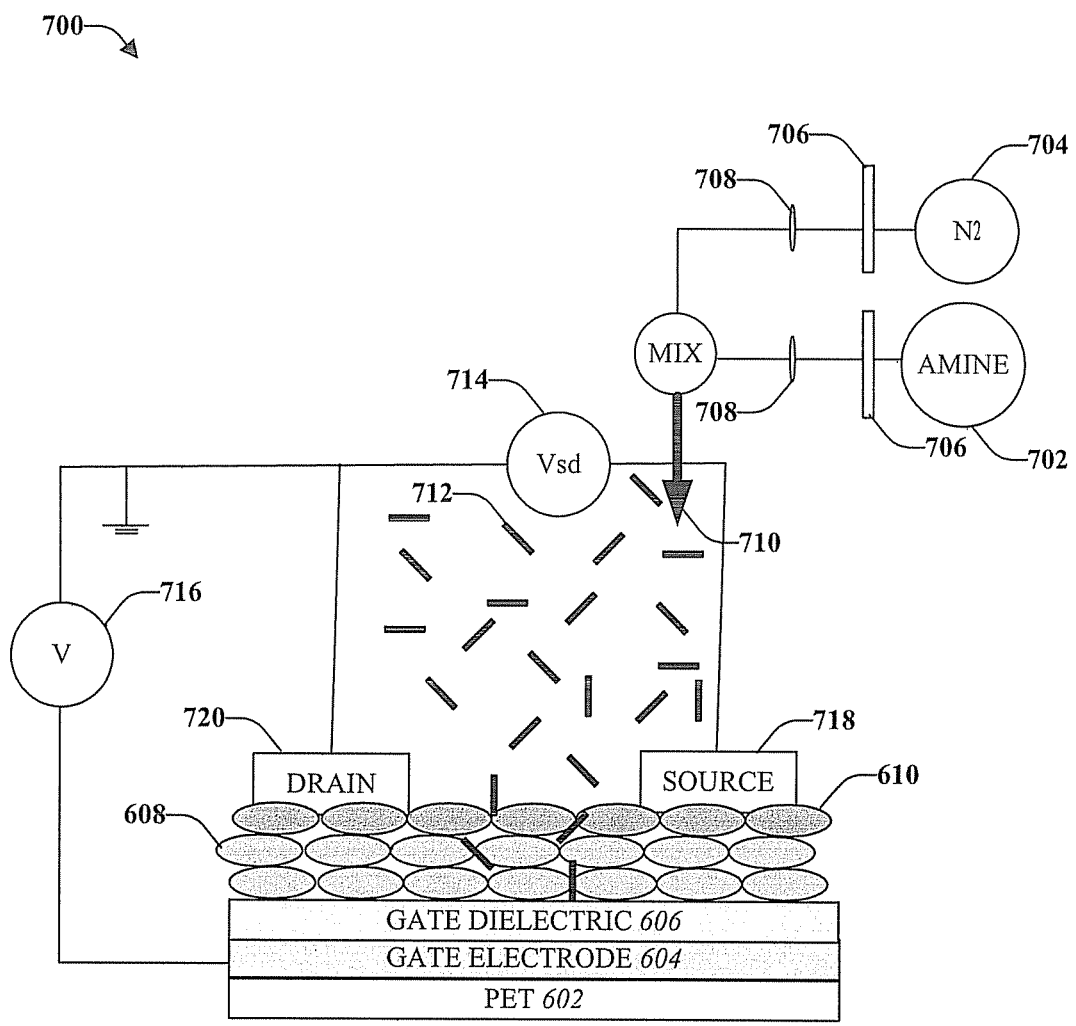
FIG. 7 is a schematic block diagram of a system for evaluating sensing properties of an amine sensor

Referring now to FIG. 7, illustrated is a schematic block diagram of a system 700 for evaluating sensing properties of an amine sensor (e.g., amine sensor 600 as described above). System 700 allows the direct delivery of amine 702 gas (e.g., from certified cylinders) to the sensor. For example, certified sensors can be connected to a gas delivery system by means of valves (e.g., four independent valves) to avoid contamination. Nitrogen 704 gas can be used to dilute amine test gasses and/or as a carrier gas. The amine test gasses and nitrogen can be mixed via flow meters 706 and valves 708. The amine test gasses and nitrogen can be delivered onto the sensor (e.g., amine sensor 600) at a constant flow rate (e.g., 200 sccm).

The sensor (e.g., the amine sensor 600 described above, an ultrathin P3HT based PTFT) can be exposed to each gas at different concentrations through a nozzle 710. For example, the nozzle can be of ca. 3 mm in diameter allocated on the device active layer. For example, an amine gas 712 can be delivered through the nozzle 710 and detected by the sensor (e.g., sensor 600).

Figure 8:
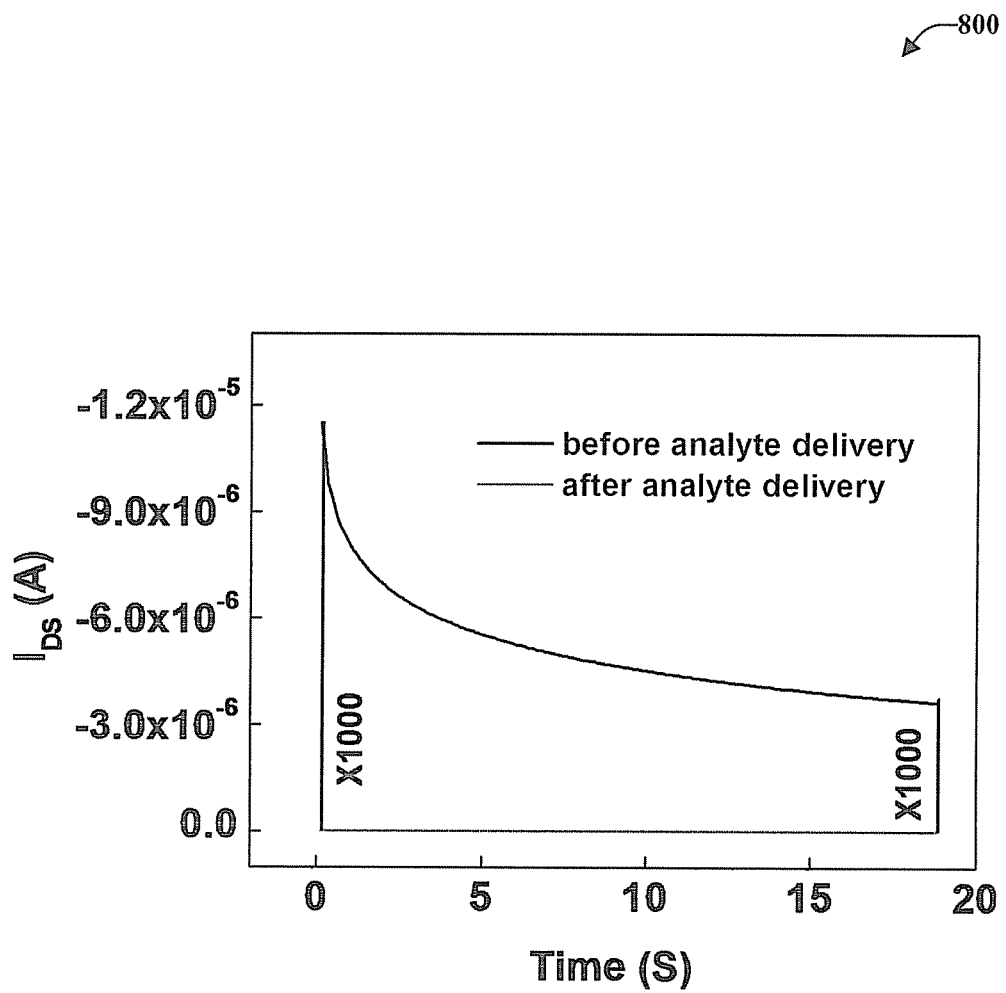
FIG. 8 is a plot illustrating a typical a source-drain current ($I_{ds}$) transient response curve for an amine sensor.

Sensing properties of the sensor (e.g., sensor 600) were evaluated based on source-drain current ($I_{DS}$). $I_{DS}$ was obtained at fixed source-drain voltage ($V_{SD}$) 714 and fixed source-gate voltage (V) 716 while exposing the sensor (e.g. sensor 600) to the test mixtures for 20 seconds. The source 718 and drain 720 are schematically illustrated on the sensor. Referring now to FIG. 8, illustrated is a plot 800 showing typical $I_{DS}$ transient response curves under 50 parts per million amine.

After exposing the sensor (e.g., sensor 600) to the test mixture, the sensor was exposed to pure nitrogen flux for 120 seconds. The sensing properties of the sensor (e.g., sensor 600) were evaluated also through the measurements of the device transfer characteristic curves (e.g., $I_{DS}$ vs. $V_g$) in nitrogen and, subsequently, in analyte atmosphere.

The amine sensors described herein (e.g., PTFT sensor 600) have a very high sensitivity for amines. For example, the amine sensor described herein can detect concentrations of amines at a parts per billion concentration level. Accordingly, sensors described herein have potential applications in the food industry. For example, sensors described herein can be utilized as a food safety tag.

The easy and inexpensive fabrication methods described in FIG. 1 and FIG. 3 makes the PTFT amine sensors described herein excellent candidates for use as disposable sensors. For example, the amine sensors described herein can be utilized as food safety tags within food packaging. Persons having ordinary skill in the art will understand that food safety is just an exemplary application for the sensors described herein. The amine sensors can be used in any application to detect amines. For example, the amine sensors described herein can, additionally or alternatively, be utilized in environmental monitoring applications.

Figure 9:
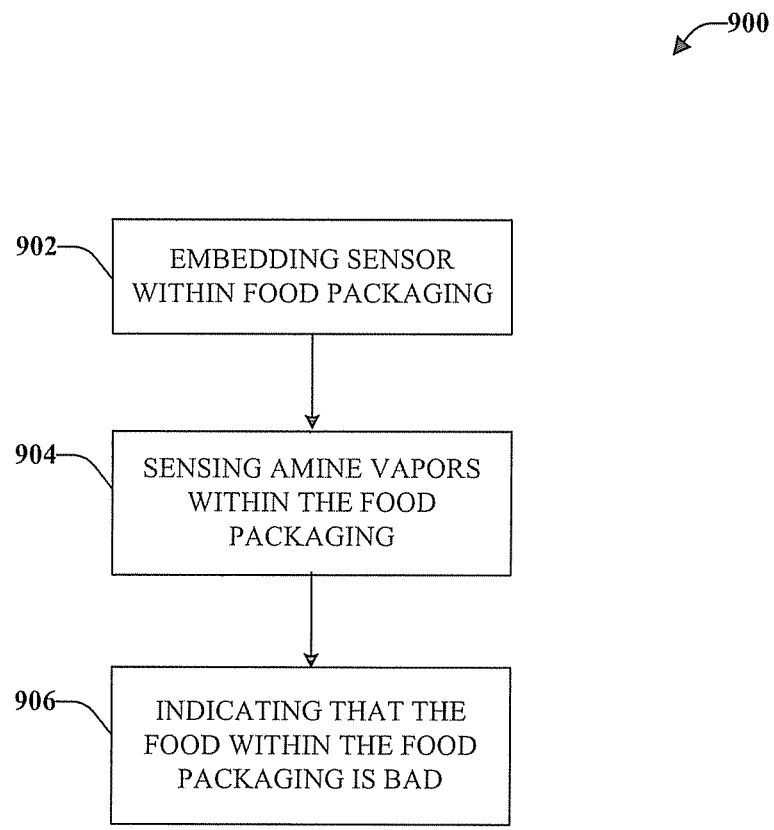
FIG. 9 is a schematic process flow diagram of a method for utilizing an ultrathin film polymer based amine sensor to facilitate food safety.

Referring now to FIG. 9, illustrated is a method of sensing amine vapors within food packaging. Amine vapors within food packaging can indicate, for example, that the food within the packaging is bad. For example, amine vapors within the food packaging can indicate that consumption of the food within the packaging may cause food poisoning.

At element 902, an amine sensor (e.g. sensor 600) is embedded within food packaging. For example, the amine sensor can be a disposable food safety tag. At element 904, the sensor can sense amine vapors within the food packaging. The sensor can detect amine vapors at low concentrations. For example, the sensor can sense amine vapors at concentrations on the order of parts per billion. For example, sensor 600 can exhibit a sensitivity of less than 1000 parts per billion. According to a further example, sensor 600 can exhibit a sensitivity of less than 500 parts per billion. According to another example, sensor 600 can exhibit a sensitivity of less than 100 parts per billion. Further, for example, sensor 600 can exhibit a sensitivity of less than 50 parts per billion.

At element 906, the sensor can indicate that the food within the packaging is bad due to its detection of the amine vapor. For example, the sensor can facilitate a visual indication that the food is bad. The visual indication can be, for example, a color change. Although a visual indication is described, it will be understood by a person having ordinary skill in the art that a visual indication is merely exemplary. The sensor can facilitate any alert indicating that the food is bad. For example, the alert can be an audio alert, a visual alert, a tactile alert, or the like. According to an aspect the sensor can indicate that the food within the food packaging is bad when the amine vapors sensed exceeds a pre-defined risk with respect to the food being spoiled.

With respect to any figure or numerical range for a given characteristic, a figure or a parameter from one range may be combined with another figure or a parameter from a different range for the same characteristic to generate a numerical range.

Other than the operating examples, or where otherwise indicated, all numbers, values, and/or expressions referring to quantities of ingredients, reaction conditions, etc., used in the specification and claims are to be understood as modified in all instances by the term "about."

The embodiments as disclosed and described in the application are intended to be illustrative and explanatory, and not limiting. Modifications and variations of the disclosed embodiments, for example, of the processes and apparatuses employed (or to be employed) as well as of the compositions and treatments used (or to be used), are possible; all such modifications and variations are intended to be within the scope of this application.

What has been described above includes examples of the subject innovation. It is, of course, not possible to describe every conceivable combination of components or methods for the purpose of describing the subject innovation. One having ordinary skill in the art, however, can recognize that many further combinations and permutations of the disclosed information are possible. Accordingly, the disclosed information is intended to embrace all such modifications, alterations and variations that fall within the spirit and scope of the applications and the appended claims.

Furthermore, to the extent that the term "includes," "has," "involves," or variants thereof are used either in the detailed description or the claims, such terms are intended to be inclusive in a manner similar to the term "comprising" as "comprising" is interpreted when employed as a transitional word in a claim.

What is claimed is:

1. A method, comprising:
   fabricating a substrate; and
   depositing a film of poly-3-hexyl thiophene (P3HT) on an octadecylphosphonic acid (ODPA) monolayer of the substrate to form a top layer of a gas sensor for sensing gas vapors.

2. The method of claim 1, wherein the fabricating the substrate further comprises fabricating an ODPA/aluminum oxide ($Al_2O_3$)/polyethylene terephthalate (PET) substrate.

3. The method of claim 1, wherein the depositing the film of P3HT comprises depositing the film of P3HT according to a solution process.

4. The method of claim 1, wherein the depositing the film of P3HT further comprises depositing the film of P3HT with a thickness on an order of nanometers.

5. The method of claim 1, wherein the depositing the film of P3HT further comprises depositing the film of P3HT with a thickness between approximately one and approximately 60 nanometers.

6. The method of claim 1, wherein the depositing the film of P3HT further comprises depositing the film of P3HT with a thickness between approximately one and approximately 15 nanometers.

7. The method of claim 1, wherein the depositing the film of P3HT further comprises depositing the film of P3HT with a thickness between approximately 1.5 and approximately 3 nanometers.

8. The method of claim 1, wherein the depositing the film of P3HT further comprises depositing the film of P3HT with a thickness between approximately two and approximately three nanometers.

9. The method of claim 1, wherein the sensing the gas vapors further comprises sensing amine vapors with the gas sensor.

10. The method of claim 1, wherein the sensing the gas vapors further comprises sensing amine vapors with the gas sensor with a sensitivity to amine concentrations less than 500 parts per billion.

11. The method of claim 1, wherein the sensing the gas vapors further comprises sensing amine vapors with the gas sensor with a sensitivity to amine concentrations less than 100 parts per billion.

12. The method of claim 1, wherein the sensing the gas vapors further comprises sensing amine vapors with the gas sensor with a sensitivity to amine concentrations less than 50 parts per billion.

13. The method of claim 1, wherein the means for depositing the film of P3HT further comprises means for depositing the film of P3HT via a solution process.

14. A polymer thin film transistor amine sensor, comprising:
 a substrate; and
 a film of poly-3-hexyl thiophene (P3HT) that is formed on an octadecylphosphonic acid (ODPA) monolayer of the substrate and as a top layer of the polymer thin film transistor amine sensor,
 wherein the polymer thin film transistor amine sensor has a sensitivity to amine vapors with a particular concentration.

15. The polymer thin film transistor amine sensor of claim 14, wherein the substrate is an ODPA/aluminum oxide ($Al_2O_2$)/polyethylene terephthalate (PET) substrate.

16. The polymer thin film transistor amine sensor of claim 15, wherein the film of P3HT is deposited on the ODPA/$Al_2O_3$/PET substrate.

17. The polymer thin film transistor amine sensor of claim 14, wherein the film of P3HT has a film thickness between approximately one and approximately 60 nanometers.

18. The polymer thin film transistor amine sensor of claim 14, wherein the film of P3HT has a film thickness between approximately two and approximately three nanometers.

19. The polymer thin film transistor amine sensor of claim 14, wherein the particular concentration is a concentration of less than 600 parts per billion.

20. The polymer thin film transistor amine sensor of claim 14, wherein the particular concentration is a concentration of less than 50 parts per billion.

21. A system, comprising:
 means for fabricating a substrate; and
 means for depositing a film of poly-3-hexyl thiophene (P3HT) on an octadecylphosphonic acid (ODPA) monolayer of the substrate to form a top layer of a gas sensor for sensing gas vapors.

* * * * *